US011584278B2

(12) United States Patent
Tait et al.

(10) Patent No.: US 11,584,278 B2
(45) Date of Patent: Feb. 21, 2023

(54) VEHICLE SEAT WITH A THERMAL MASSAGE SYSTEM

(71) Applicant: FAURECIA AUTOMOTIVE SEATING, LLC, Auburn Hills, MI (US)

(72) Inventors: Shaun D. Tait, Troy, MI (US); Anne-Isabelle Mallet-Da Costa, Étréchy (FR)

(73) Assignee: FAURECIA AUTOMOTIVE SEATING, LLC, Auburn Hills, MI (US)

( * ) Notice: Subject to any disclaimer, the term of this patent is extended or adjusted under 35 U.S.C. 154(b) by 407 days.

(21) Appl. No.: 16/834,646

(22) Filed: Mar. 30, 2020

(65) Prior Publication Data

US 2021/0300224 A1    Sep. 30, 2021

(51) Int. Cl.
| | |
|---|---|
| *B60N 2/00* | (2006.01) |
| *B60N 2/90* | (2018.01) |
| *B60N 2/56* | (2006.01) |
| *B60N 2/58* | (2006.01) |
| *A61H 9/00* | (2006.01) |
| *A61F 7/08* | (2006.01) |
| *A61F 7/00* | (2006.01) |

(52) U.S. Cl.
CPC ............... *B60N 2/976* (2018.02); *A61F 7/08* (2013.01); *A61H 9/0078* (2013.01); *B60N 2/5685* (2013.01); *B60N 2/58* (2013.01); *A61F 2007/0071* (2013.01); *A61F 2007/0088* (2013.01); *A61H 2201/0149* (2013.01); *A61H 2201/0207* (2013.01); *A61H 2201/1654* (2013.01); *A61H 2201/5002* (2013.01); *B60N 2/914* (2018.02)

(58) Field of Classification Search
CPC ........ B60N 2/58; B60N 2/5685; B60N 2/976; B60N 2/914; A61F 7/08; A61F 2007/0088; A61F 2007/0071; A61H 9/0078; A61H 2201/1623; A61H 2201/0207; A61H 2203/0431; A61H 2201/5007; A61H 2201/1654; A61H 2201/5002; A61H 2201/1633; A61H 2201/0149; A61H 2201/5046; A61H 2201/0228; A61H 2201/5035
See application file for complete search history.

(56) References Cited

U.S. PATENT DOCUMENTS

| | | | |
|---|---|---|---|
| 8,979,191 B2 | 3/2015 | Friderich et al. | |
| 9,848,814 B2 * | 12/2017 | Benson | B60N 2/002 |
| 11,173,818 B1 * | 11/2021 | Migneco | B60N 2/5671 |
| 2014/0207333 A1 * | 7/2014 | Vandivier | B60N 2/976 |
| | | | 701/36 |

(Continued)

FOREIGN PATENT DOCUMENTS

DE    102012000445 A1    9/2012

Primary Examiner — Chi Q Nguyen
(74) Attorney, Agent, or Firm — Reising Ethington P.C.

(57) ABSTRACT

A seat includes a seat bottom and a seat back. At least one of the seat bottom and the seat back includes a trim cover having a seating surface and a plurality of individually-controllable massage elements underlying the trim cover. Each of the plurality of individually-controllable massage elements has a surface facing the trim cover, wherein at least a portion of the surface includes a heating layer selectively configured to generate heat.

11 Claims, 3 Drawing Sheets

(56) References Cited

U.S. PATENT DOCUMENTS

| | | | |
|---|---|---|---|
| 2015/0126916 A1* | 5/2015 | Hall | A61H 9/0078 |
| | | | 601/149 |
| 2018/0015853 A1* | 1/2018 | Lem | B60N 2/976 |
| 2018/0111527 A1* | 4/2018 | Tait | B60N 2/5635 |
| 2018/0325264 A1 | 11/2018 | Gallagher et al. | |
| 2019/0031061 A1* | 1/2019 | Reith | B60N 2/5635 |
| 2019/0038147 A1 | 2/2019 | Perraut et al. | |
| 2019/0344043 A1* | 11/2019 | Migneco | B60N 2/0244 |
| 2021/0016686 A1* | 1/2021 | Yetukuri | B60N 2/5621 |

* cited by examiner

VEHICLE SEAT WITH A THERMAL MASSAGE SYSTEM

TECHNICAL FIELD

The present disclosure is related generally to seating and, more particularly, to vehicle seating with a thermal massage system.

BACKGROUND

Vehicle seats can be configured with comfort adjustment systems that can influence the contour of the seat, provide massage capabilities, and control the temperature of the seating surface.

For example, U.S. Pat. No. 8,979,191 to Friderich et al. discloses a vehicle seat with a massage device and a seat climate control system, both of which can be controlled using a control device. The massage device includes a plurality of pressurizable elements integrated into the pad, which can be controlled separately to influence the contour of the seat.

SUMMARY

In accordance with one or more embodiments, a seat includes a seat bottom and a seat back. At least one of the seat bottom and the seat back includes a trim cover having a seating surface and a plurality of individually-controllable massage elements underlying the trim cover. Each of the plurality of individually-controllable massage elements having a surface facing the trim cover, wherein at least a portion of the surface includes a heating layer selectively configured to generate heat.

In some embodiments, the heating layer is at least one of an electrically conductive coating, a laminated resistive heater, a flex heater, and a carbon heater.

In some embodiments, the heating layer defines a contact region on the surface of each of the plurality of individually-controllable massage elements that, when activated, applies pressure respectively to a seat occupant.

In some embodiments, the plurality of individually-controllable massage elements are pressurizable elements configured to activate pneumatically or electro-pneumatically.

In some embodiments, the plurality of individually-controllable massage elements are operably coupled to a controller configured to selectively and independently activate the plurality of individually-controllable massage elements and the heating layer.

In some embodiments, the plurality of individually-controllable massage elements are inflatable bladders.

In some embodiments, the plurality of individually-controllable massage elements are hollow bodies configured to be pressurized with a medium.

In some embodiments, the seat includes a heat mat underlying the trim cover.

In some embodiments, the heat mat is a carbon or flex heater.

In some embodiments, the heat mat is overlying the plurality of individually-controllable massage elements.

In some embodiments, the heat mat includes apertures at locations in which the heat mat overlies the plurality of individually-controllable massage elements.

In some embodiments, the apertures are slits positioned along at least a portion of a periphery of the plurality of individually-controllable massage elements enabling movement thereof relative to the heat mat.

In some embodiments, the apertures are openings extending along and exposing the surface of the plurality of individually-controllable massage elements through the openings.

In some embodiments, the seat includes a foam cushion underlying the trim cover, the foam cushion having a first side facing the trim cover and an opposite second side.

Various aspects, embodiments, examples, features and alternatives set forth in the preceding paragraphs, in the claims, and/or in the following description and drawings may be taken independently or in any combination thereof. For example, features disclosed in connection with one embodiment are applicable to all embodiments in the absence of incompatibility of features.

BRIEF DESCRIPTION OF THE DRAWINGS

Exemplary embodiments will hereinafter be described in conjunction with the appended drawings, wherein like designations denote like elements, and wherein.

DETAILED DESCRIPTION

Figure 1:
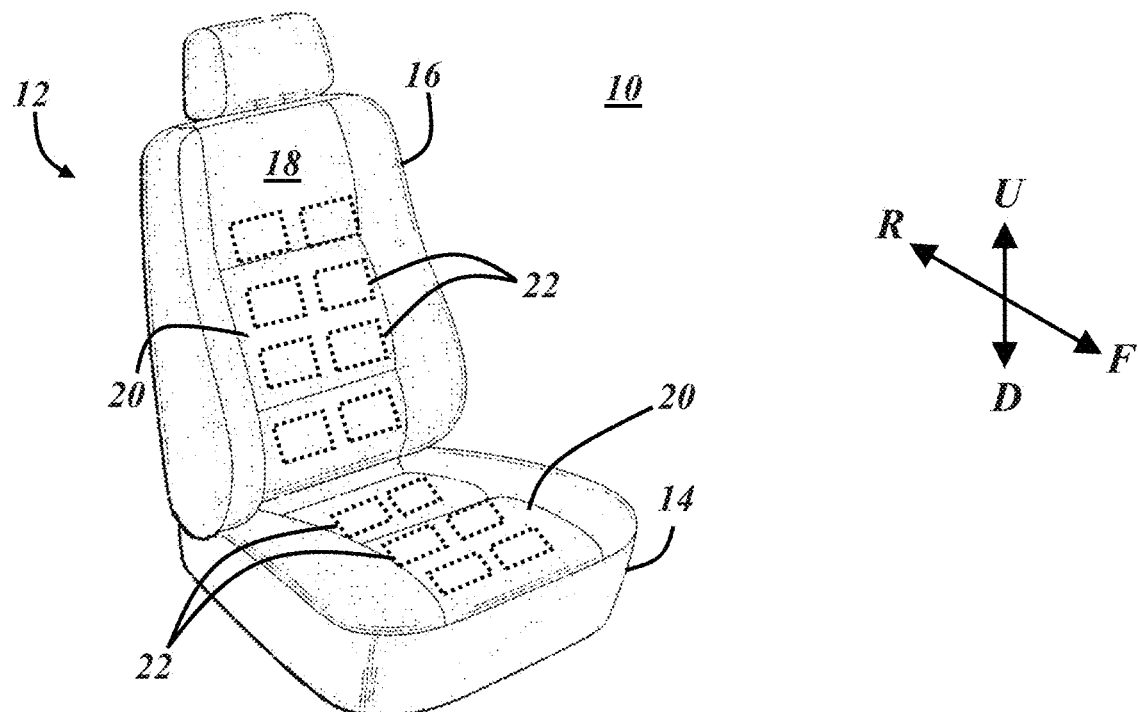
FIG. 1 is a perspective view of an embodiment of a vehicle seat equipped with a thermal massage system.

A perspective view of an exemplary seat 12 of a seating system 10 is shown in FIG. 1. Seating system 10 may be configured for use in vehicular and/or non-vehicular applications. Vehicular applications may include land vehicles such as cars, trucks, and trains, and non-land vehicles such as aircraft or marine vessels. Non-vehicular applications may include home or office furniture such as chairs or the like. Herein, seating system 10 will be described as for use in a vehicle and seat 12 will be understood as being a vehicle seat.

FIG. 1 illustrates an exemplary vehicle seat 12 adapted for installation in the passenger cabin of a vehicle via rails along the underside of the seat or other suitable attachment features. The seat 12 includes a seat bottom 14 and a seat back 16 extending from the seat bottom. Forward (F) and rearward (R) directions are designated in FIG. 1 and may be referred to as longitudinal directions. Upward (U) and downward (D) directions may be referred to as vertical directions, while left and right may be referred to as transverse directions. These directions are with respect to the seat 12 and not necessarily with the vehicle in which the seat is installed. The seat 12 presents a seating surface 18 in the form of an exterior surface of a trim cover 20. Each of the seat bottom 14 and the seat back 16 includes a portion of the seating surface 18, which is in contact with a seat occupant. The trim cover 20 may be formed from any material or combination of materials including, without limitation: leather, woven or knit fabrics, polymeric materials such as polyvinyl chloride (PVC) or polyurethane.

As used herein, the terms "underlying" and "overlying" are in relation to a reference frame in which the seating surface 18 is the topmost surface. For example, an underlying layer in the seat back 16 is generally located rearward of the portion of the seating surface 18 provided by the seat back 16, and an underlying layer in the seat bottom 14 is generally located beneath the portion of the seating surface 18 provided by the seat bottom 14.

As shown in phantom in FIG. 1, the thermal massage system of the seat 12 includes a plurality of massage elements 22 underlying the trim cover 20. In this particular example, the massage elements 22 are arranged to the left and right of a vertical symmetry plane along the seat back 16 such that when activated, massaging pressure is applied to the muscle groups located along the spine of the seat occupant. The massage elements 22 located in the seat bottom 14 are similarly arranged to the left and right of a symmetrical plane in the seat bottom 14 to provide massaging pressure when activated along the typical location of the legs of the seat occupant.

The massage elements 22 in FIG. 1 are arranged for purposes of illustration to correspond with general anatomical locations of a seat occupant's major muscle groups. However, the placement and arrangement of the massage elements 22 may vary depending on the geometrical and structural configuration of the seat 14, the number, size, and shape of the massage elements 22, and the type of massage element 22. The massage elements 22 may be used in only one of the seat bottom 14 or the seat back 16, or may be used in both the seat bottom 14 and the seat back 16. The massage elements 22 may be arranged to operate independently, or may be arranged to operate in groups or zones, as described below.

In an exemplary seat 12, the plurality of massage elements 22 are hollow bodies configured to be pressurized with a medium. One example of a hollow-bodied element is a bladder. Other types of massage elements are possible, including but not limited to, massage batters and actuator-type massage mechanisms. Thus, while other configurations are possible, the following description and illustrations are directed to a seat 12 wherein the plurality of massage elements 22 are bladders. The hollow bodies of the bladders may be pressurized with a medium, e.g., pressurized air. The bladders can be pneumatically or electro-pneumatically pressurized by individual lines (not shown).

Figure 2:
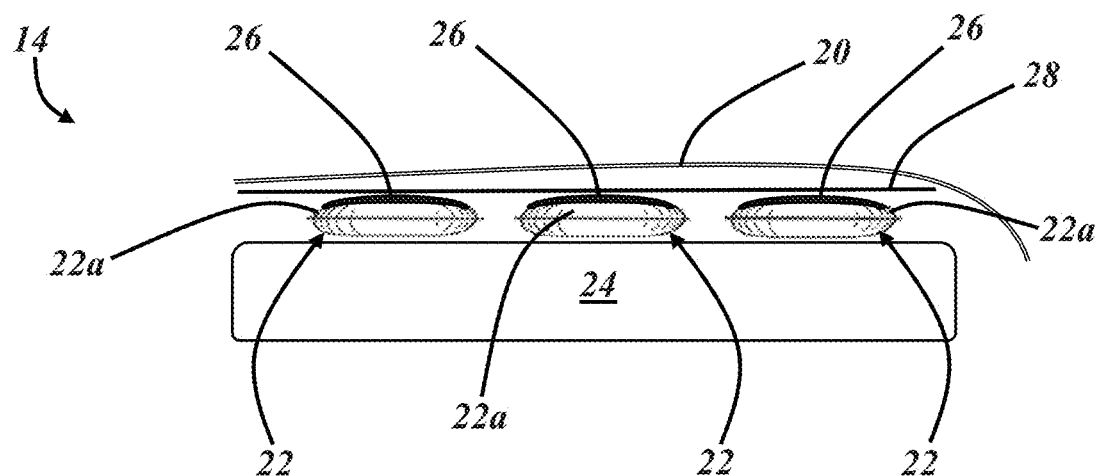
FIG. 2 is a side cross-sectional view of the seat bottom of the vehicle seat illustrating an example of the thermal massage system.

FIG. 2 is a cross-sectional side view of the seat bottom 14 shown in FIG. 1. The seat bottom 14 includes a foam cushion 24 underlying the trim cover 20 and supporting the plurality of massage elements 22. The foam cushion 24 has a first side facing the trim cover 20 and an opposite second side. As illustrated in FIG. 2, each of the plurality of massage elements 22 includes a surface 22a facing the trim cover 20. A heating layer 26 is disposed over at least a portion of the surface 22a forming a contact region such that, when activated, pressure and/or heat are applied to the seat occupant at the contact region. The size and shape of the contact region may vary depending on the type of massage element and heating layer. The heating layer 26 is configured to selectively generate heat such that the heat is locally combined with the pressure acting on the seat occupant via pressurization of the massage elements 22. This centralized combination of heat and massage action emulates the feeling of a hot stone massage. The heating layer 26 may include any heater that can be adhered, bonded, or otherwise attached to at least a portion of the surface 22a of the massage element 22 enabling localization of the heat in combination with the massaging action of the massage elements 22. By way of example, the heating layer 26 may include an electrically conductive coating, a laminated resistive heater, a thin-film printed heater including conductive tracks, a flex heater, and a carbon-based heater, to name a few.

Figure 3:
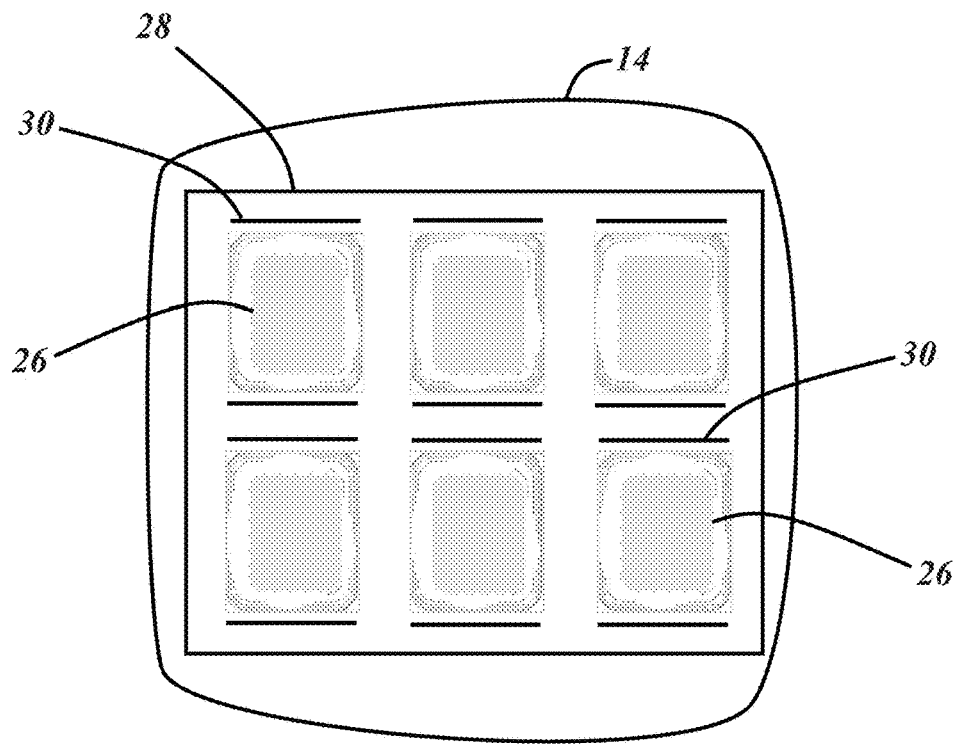
FIG. 3 is a top view of the seat bottom of the vehicle seat with the trim cover omitted to show apertures in the seat mat configured as slits.
Figure 4:
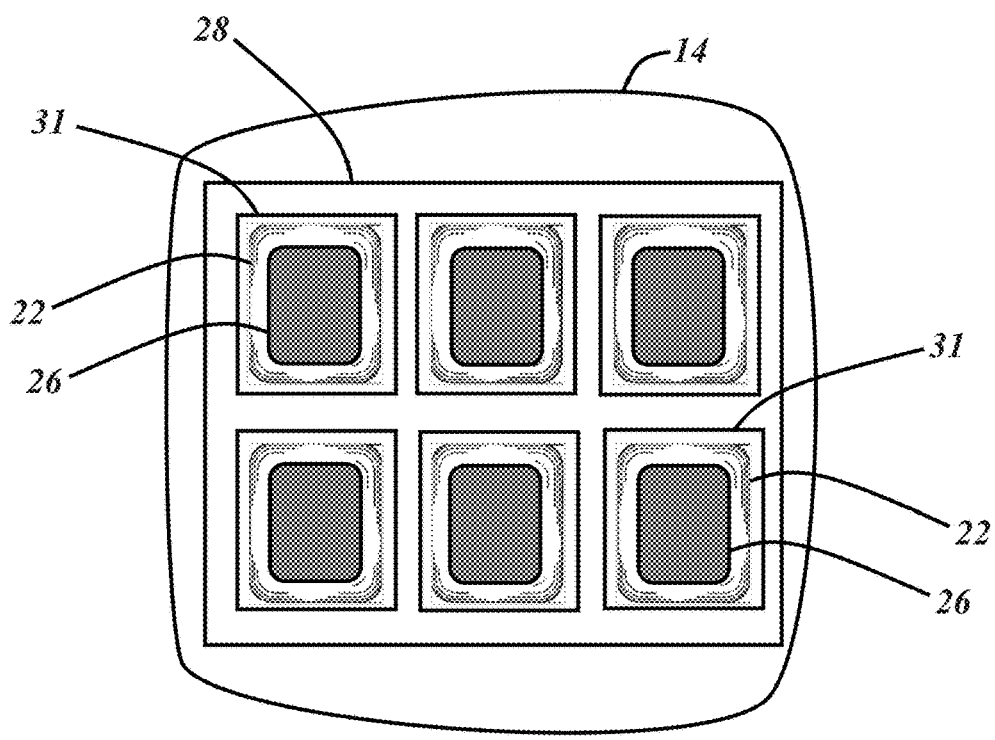
FIG. 4 is a top view of the seat bottom of the vehicle seat with the trim cover omitted to show apertures in the seat mat configured as openings.

The seating system 10 may further include a heat mat 28 underlying the trim cover 20. The heat mat 28 is a seat heater having heating elements in the form of heating wires. Alternatively, the heat mat may be formed as a carbon or flex heater. Other configurations are also possible. The heat mat 28 includes apertures at locations in which the heat mat 28 overlies the massage elements 22. In one example, as shown in FIG. 3 (seat cover omitted), the apertures are slits 30 positioned along at least a portion of a periphery of the massage elements 22 enabling movement of the massage elements 22 relative to the heat mat 28 as the massage elements are activated. In another example, as shown in FIG. 4 (seat cover omitted), the apertures are openings 31 extending along and exposing the surface 22a of the massage elements 22 through the openings 31 providing unobstructed movement of the massage elements 22 while activated.

Figure 5:
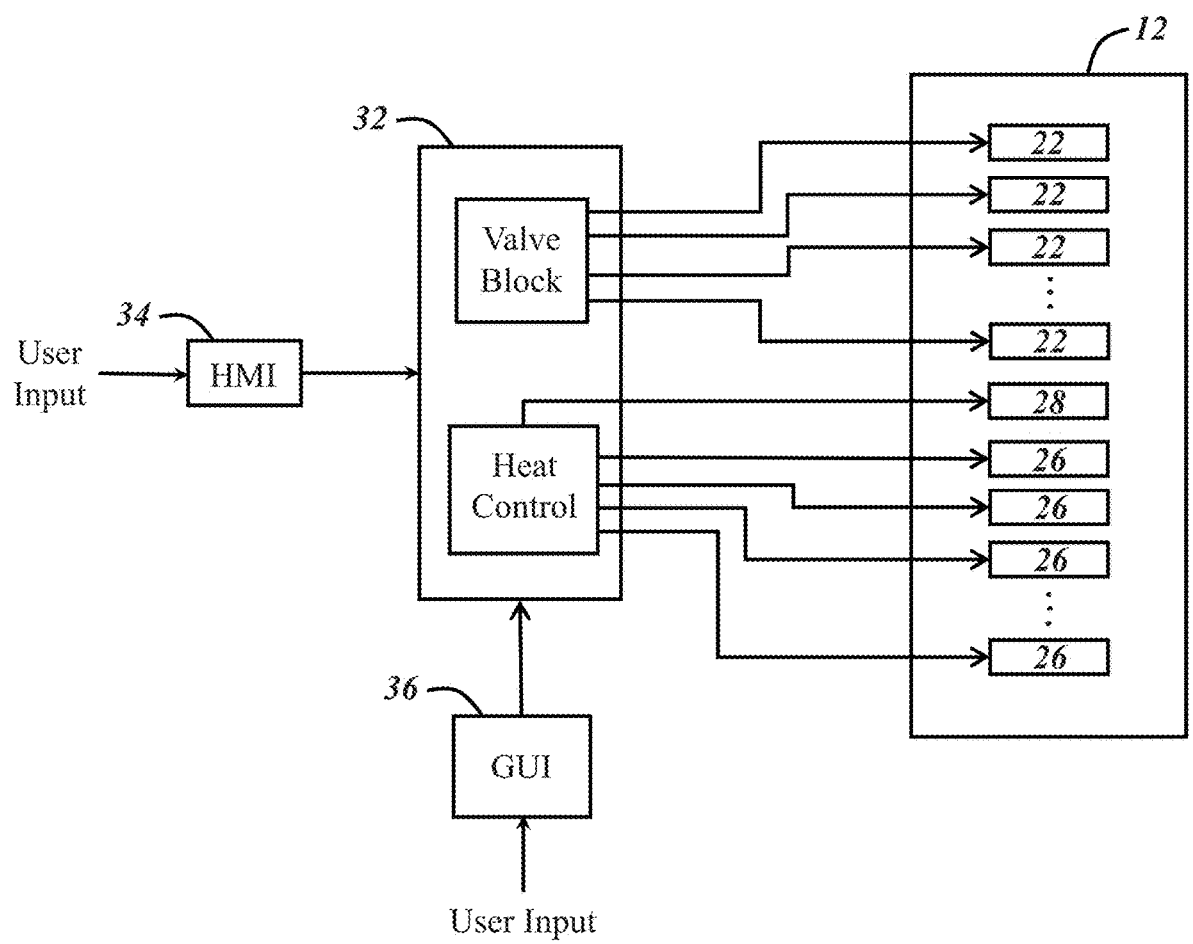
FIG. 5 is a block diagram of a control architecture for the vehicle seat shown in FIG. 1

FIG. 5 illustrates an exemplary control architecture for seating system 10 and includes a controller 32. The plurality of massage elements 22 are configured to operate independently of one another via the controller 32, and more particularly, through valve block 32a. In this way, the massage elements 22 can be configured to function alone or in groups (i.e., subsets) to provide targeted stimulation. Similarly, the heating layers 26 are configured to operate independently of one another via the controller 32, and more particularly, through heat controller 32b. In this way, the heat layers 26 can be configured to operate alone, in groups (i.e., subsets), in unison with the plurality of massage elements 22, or independent from the massage elements 22. The controller 32 is further configured to control the functionality of the heat mat 28 independently from both the massage elements 22 and the heat layers 26.

The selection of the plurality of massage elements 22 for activation and the temperature settings for the heating layers 26 may be carried out in various ways in seating system 10. One way involves a user providing manual input to controller 32. In this regard, seating system 10 further includes an input device in the form of a human-machine interface (HMI) device 34 in communication with controller 32. A user such as a seat occupant accesses the HMI device 34 to provide manual input to controller 32. For instance, HMI device 34 may include a touchscreen, knobs, buttons, microphone for voice commands, etc. The seat occupant accesses the HMI device 34 to select which massage elements 22 are to be activated, the temperature settings of the heating layers 26 that are to be activated, the duration of activation, and the like. Controller 32 in turn activates the massage elements 22, the heating layers 26, and the heat mat 28 according to the user input.

A user may also select a pre-programmed massage program by accessing an input device in communication with controller 32. In this regard, seating system 10 further includes a graphical user interface (GUI) 36 in communication with controller 32. GUI 36 is configured to display pre-programmed options for a user to view. The user accesses GUI 36 to select one of the pre-programmed options and the controller 32 in turn activates the corresponding massage elements 22 and heating layers 26.

The controllers described herein may be embodied as a single dedicated controller or may include multiple controllers, each of which may be embodied as an electronic control unit or other controller configured to perform the functions described herein. In particular, and as described further below, a controller (e.g., a controller coupled to the vehicle seat) may be configured to receive data from other system components. Each controller, also called a computer, may be embodied as any device capable of performing the functions described herein. For example, each controller may be embodied as an electronic control unit, embedded controller, control circuit, microcontroller, computing device, on-board computer, and/or any other any other computing device capable of performing the functions described herein.

An illustrative controller includes a processor, an I/O subsystem, memory, a data storage device, and communication circuitry. The controller may include other or additional components, such as those commonly found in an electronic control unit (e.g., various input/output devices), in other embodiments. Additionally, in some embodiments, one or more of the illustrative components may be incorporated in, or otherwise form a portion of, another component. For example, the memory, or portions thereof, may be incorporated in the processor.

The processor may be embodied as any type of processor capable of performing the functions described herein. For example, the processor may be embodied as a microcontroller, digital signal processor, single or multi-core processor(s), or other processor or processing/controlling circuit. Similarly, the memory may be embodied as any type of volatile or non-volatile memory or data storage capable of performing the functions described herein. In operation, the memory may store various data and software used during operation of the processor such as operating systems, applications, programs, libraries, and drivers. The memory is coupled to the processor via the I/O subsystem, which may be embodied as circuitry and/or components to facilitate input/output operations with the processor, the memory, and other components of the controller. For example, the I/O subsystem may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem may form a portion of a system-on-a-chip (SoC) and be incorporated, along with the processor, the memory, and other components of the controller, on a single integrated circuit chip.

The vehicle seat bottom 10 may include other components not explicitly illustrated in the figures, such as an overlying seat cushion and/or a decorative trim cover. In addition, in practice, a vehicle seat back may be coupled to the vehicle seat bottom 10 to form a vehicle seat.

It is to be understood that the foregoing is a description of one or more preferred exemplary embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "for example," "for instance," "such as," and "like," and the verbs "comprising," "having," "including," and their other verb forms, when used in conjunction with a listing of one or more components or other items, are each to be construed as open-ended, meaning that that the listing is not to be considered as excluding other, additional components or items. Other terms are to be construed using their broadest reasonable meaning unless they are used in a context that requires a different interpretation.

The invention claimed is:

1. A seat having a seat bottom and a seat back, at least one of the seat bottom and the seat back comprising:
   a trim cover having a seating surface;
   a plurality of individually-controllable massage elements underlying the trim cover, each of the plurality of individually-controllable massage elements having a surface facing the trim cover, wherein at least a portion of the surface facing the trim cover includes a heating layer configured to selectively generate heat; and
   a heat mat underlying the trim cover, wherein the heat mat includes apertures where the heat mat overlies the plurality of individually-controllable massage elements.

2. The seat as defined in claim 1, wherein the heating layer comprises at least one of an electrically conductive coating, a laminated resistive heater, a flex heater, and a carbon heater.

3. The seat as defined in claim 1, wherein the heating layer defines a contact region on the surface of each of the plurality of individually-controllable massage elements that, when the plurality of individually-controllable massage elements is activated, applies pressure respectively to a seat occupant.

4. The seat as defined in claim 1, wherein the plurality of individually-controllable massage elements are pressurizable elements configured to activate pneumatically or electro-pneumatically.

5. The seat as defined in claim 1, wherein the plurality of individually-controllable massage elements are operably coupled to a controller configured to selectively and independently activate the plurality of individually-controllable massage elements and the heating layer.

6. The seat as defined in claim 1, wherein the plurality of individually-controllable massage elements are inflatable bladders.

7. The seat as defined in claim 1, wherein the plurality of individually-controllable massage elements are hollow bodies configured to be pressurized with a medium.

8. The seat as defined in claim 1, wherein the heat mat is a carbon or flex heater.

9. The seat as defined in claim 1, wherein the apertures are slits positioned along at least a portion of a periphery of the plurality of individually-controllable massage elements enabling movement thereof relative to the heat mat.

10. The seat as defined in claim 1, wherein the apertures are openings extending along and exposing the surface of the plurality of individually-controllable massage elements through the openings.

11. The seat as defined in claim 1, further comprising a foam cushion underlying the trim cover, the foam cushion having a first side facing the trim cover and an opposite second side.

* * * * *